US00PP20891P3

(12) United States Plant Patent
Clark

(10) Patent No.: US PP20,891 P3
(45) Date of Patent: Mar. 30, 2010

(54) BLACKBERRY PLANT NAMED 'NATCHEZ'

(50) Latin Name: ***Rubus* spp.**
Varietal Denomination: Natchez

(75) Inventor: John Reuben Clark, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 12/152,524

(22) Filed: May 15, 2008

(65) Prior Publication Data

US 2009/0288233 P1 Nov. 19, 2009

(51) Int. Cl.
*A01H 5/00* (2006.01)

(52) U.S. Cl. ..... Plt./203

(58) Field of Classification Search ..... Plt./203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP17,162 | P3 | 10/2006 | Clark et al. |
| PP17,983 | P2 | 9/2007 | Cabrera Avalos |

*Primary Examiner*—Annette H Para
(74) *Attorney, Agent, or Firm*—Michael Best & Friedrich LLP

(57) ABSTRACT

Description and specifications of a new and distinct blackberry cultivar named 'Natchez' which originated from seed produced by a hand pollinated cross of Ark. 2005 (non-patented)×Ark. 1857 (non-patented) is provided. This new blackberry cultivar can be distinguished by its high yields, large fruit size, good fruit quality, early season fruit ripening, prolific fruiting row establishment, and healthy plants.

4 Drawing Sheets

Botanical designation: *Rubus* spp.

BACKGROUND

A new cultivar of blackberry called 'Natchez' is described herein. The new cultivar originated from a hand pollinated cross of Ark. 2005 and Ark. 1857 made in 1998. The seeds resulting from this controlled hybridization were germinated in a greenhouse in the spring of 1999 and planted in a field near Clarksville, Ark. The seedlings fruited during the summer of 2001 and one seedling, designated Ark. 2241, was selected for its early season of ripening, large fruit size, excellent fruit quality, excellent plant health, and thornless canes.

SUMMARY OF THE INVENTION

The new and distinct cultivar of blackberry originated from a hand pollinated cross of Ark. 2005 (non-patented, unreleased genotype)×Ark. 1857 (non-patented, unreleased genotype) made in 1998 and located near Clarksville, Ark. (West-Central Arkansas).

The seeds resulting from this controlled hybridization were germinated in a greenhouse in the spring of 1999 and planted in a field near Clarksville, Ark. The seedlings fruited during the summer of 2001 and one seedling, designated Ark. 2241, was selected for its early season of ripening, large fruit size, excellent fruit quality, excellent plant health, and thornless canes.

During 2001, the original plant selection was propagated asexually from root cuttings, at the above noted location, and a test row of 20 plants was established. Subsequently, larger test plantings have been established with asexually multiplied plants at the above noted location and planted at three locations in Arkansas. Additionally, the cultivar has been tested at test plots in Baxley, Ga. and Aurora, Oreg., and at each location propagation was from root cuttings from the Clarksville, Ark. test plot.

The new cultivar has been asexually multiplied annually since 2001 by the use of root cuttings and by rooting adventitious shoots from root cuttings. It forms new shoots from adventitious buds on root cuttings (per 12 cm root cutting) more readily than Ouachita (U.S. Plant Pat. No. 17,162) providing an average of 6.8 shoots compared to 1.2 for Ouachita. During all asexual multiplication, the characteristics of the original plant have been maintained and no aberrant phenotypes have appeared.

Test plantings over a wide geographic area have shown this new cultivar to be adapted to differing soil and climatic conditions. The new cultivar has been named the 'Natchez' cultivar.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR 'NATCHEZ'

Figure 1:
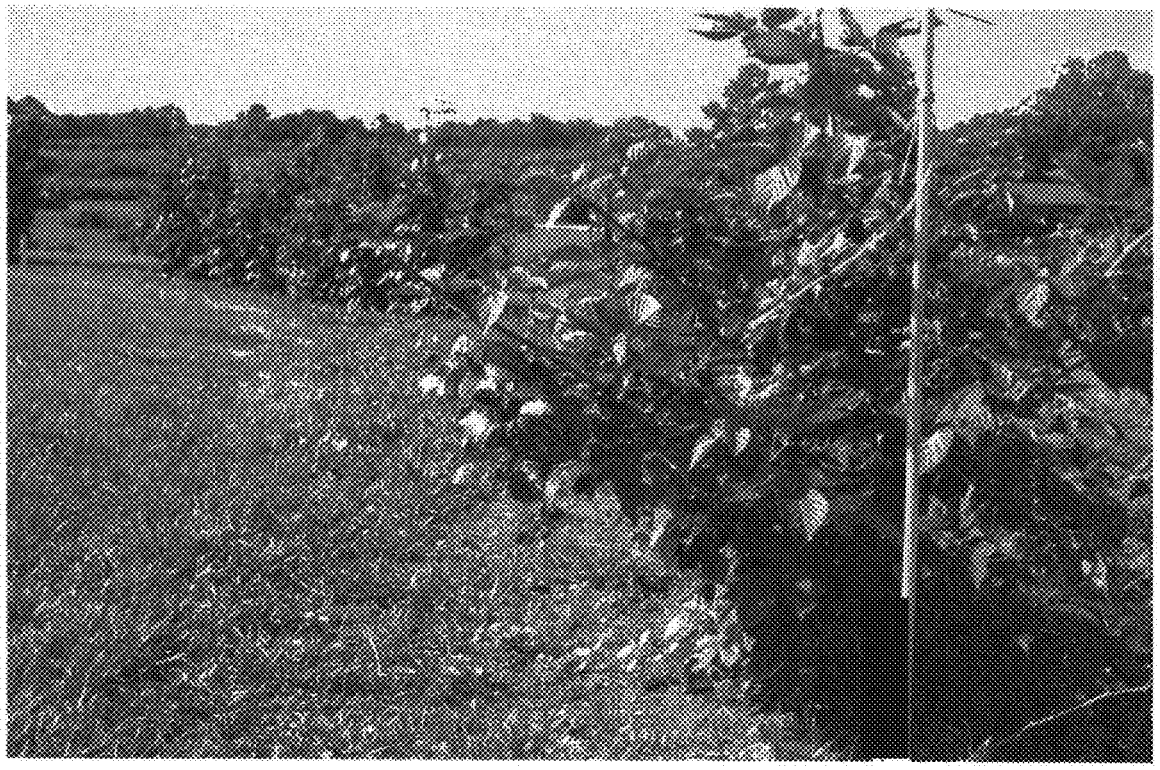
FIG. 1 is a photograph showing a blackberry plant of the cultivar 'Natchez.'
Figure 2:
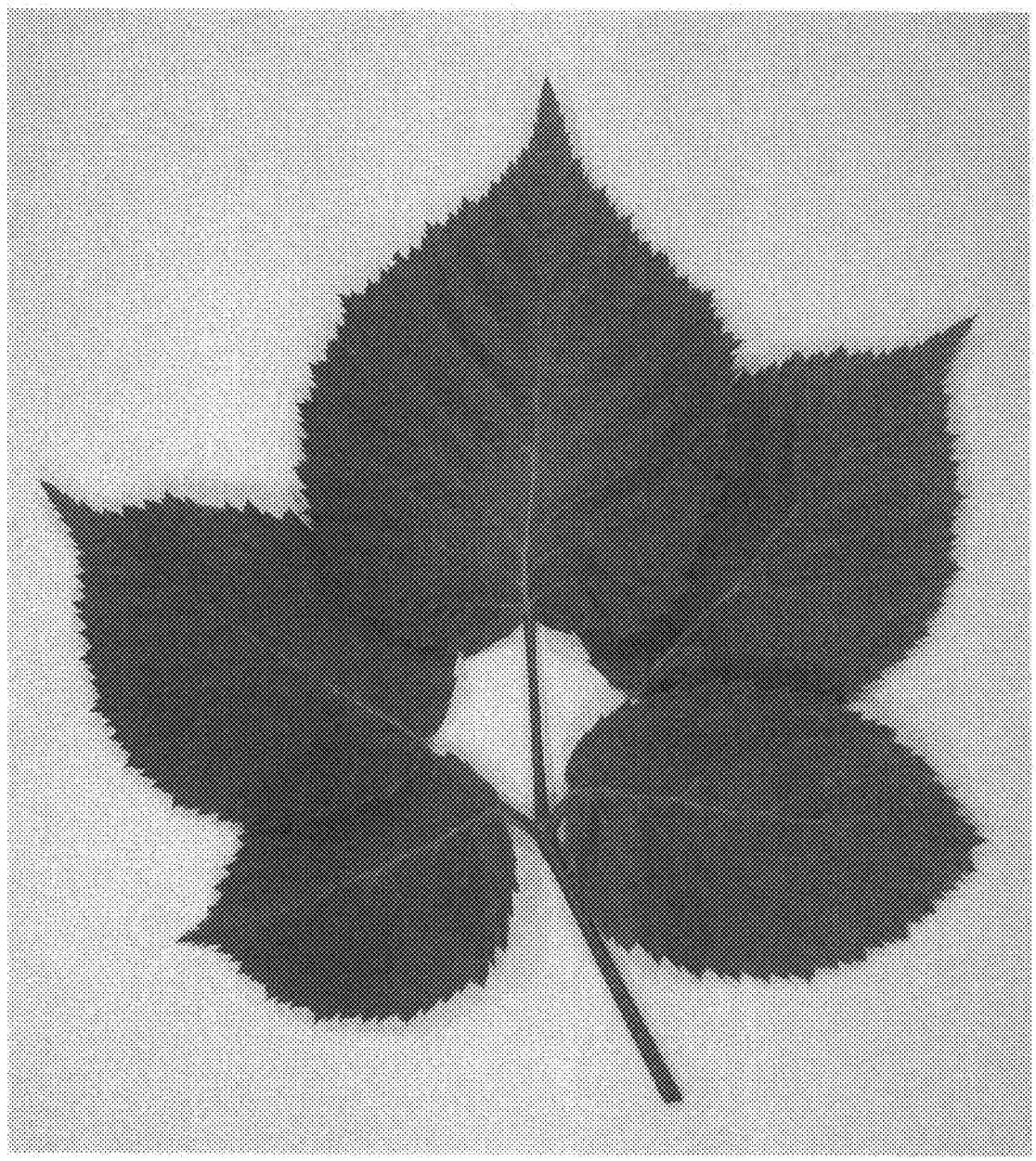
FIG. 2 is a photograph showing the upperside of a primocane leaf of the plant.
Figure 3:
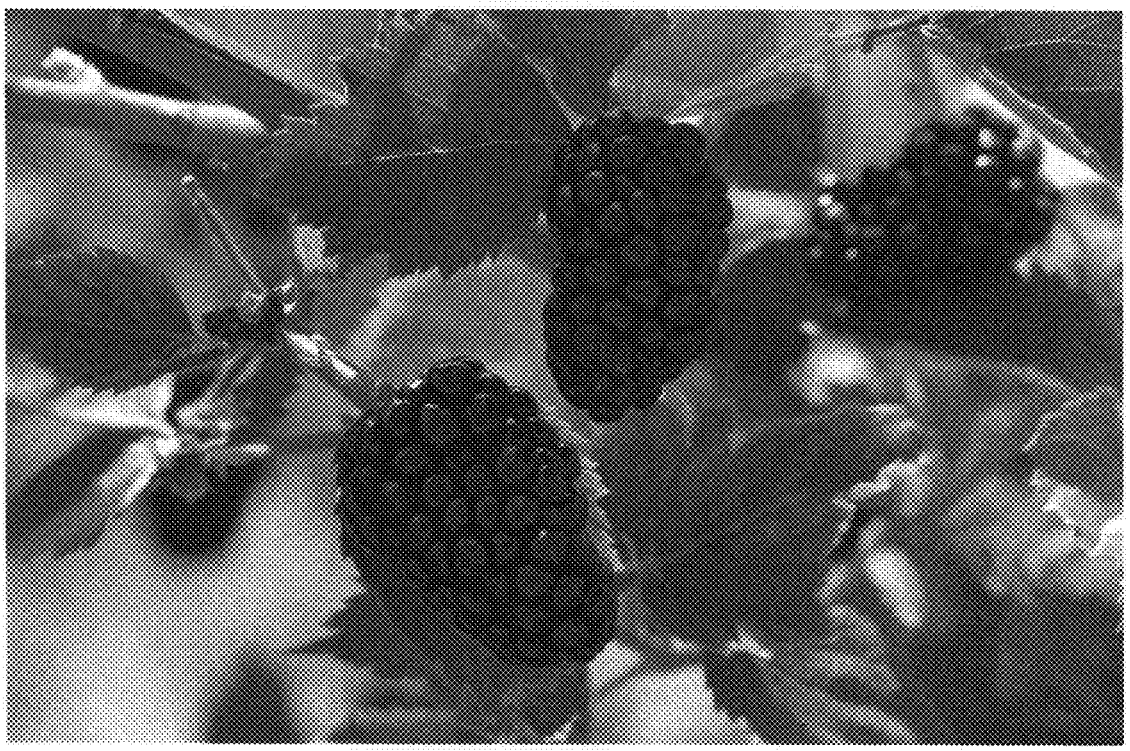
FIG. 3 is a photograph showing blackberry fruit on the plant.
Figure 4:
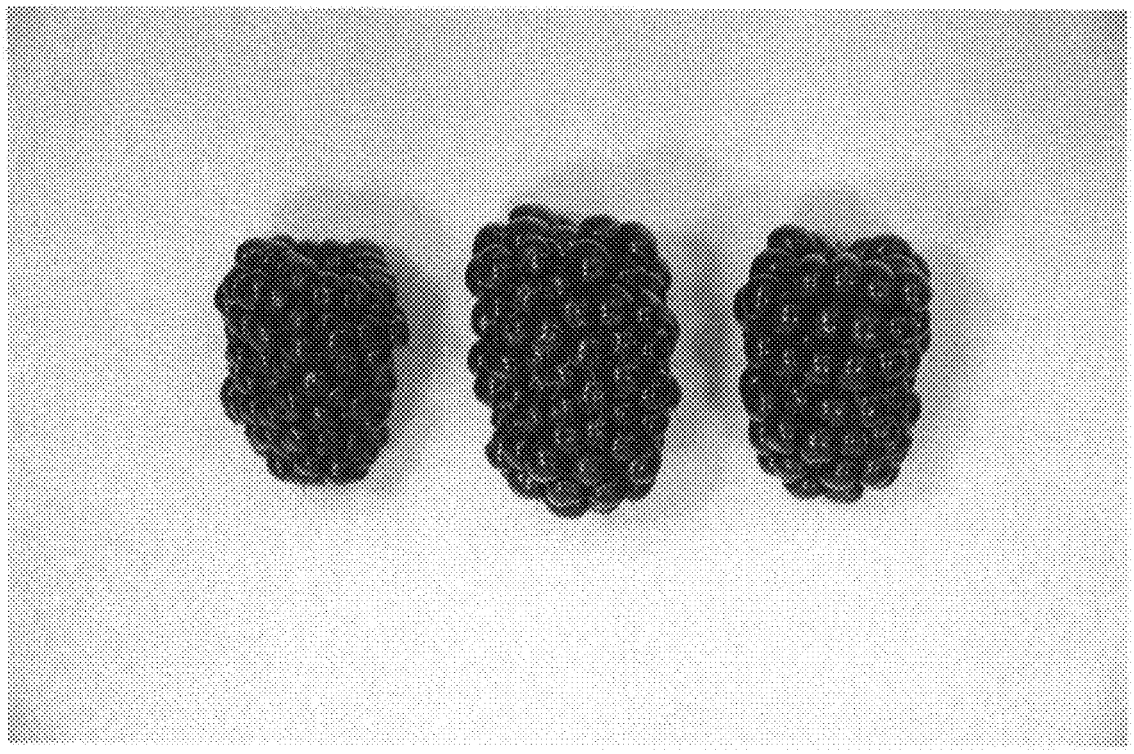
FIG. 4 is a photograph showing three blackberries from the plant.

Plants and fruit of this new cultivar differ phenotypically from its parents. The new cultivar is earlier ripening and larger in fruit size than the parent Ark. 2005, and is more productive and larger than parent Ark.1857. The new cultivar retains larger fruit size throughout the harvest season than either of the parent blackberries. Although blackberries (*Rubus* subgenus *Rubus*) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry) possibly introgressed with *R. argutus* Link. (tall blackberry). Its genes for thornlessness were derived from the British cultivar 'Merton Thornless' (non-patented), a derivative of *Rubus ulmifolius* Schott.

Plants of the new cultivar 'Natchez' are vigorous and prolific and row establishment following planting is rapid. Both primocanes and floricanes are erect to semi-erect in growth habit. The canes can be trained to a self-supporting hedgerow although it is beneficial to use a trellis with supporting wires to prevent canes from falling over due to wind or heavy fruitloads. The plants are genetically thornless, having the recessive genes for thornless derived from the cultivar Merton Thornless (non-patented). Plants and fruit are moderately resistant to anthracnose [*Elsinoe veneta* (Burkh.) Jenkins], and plants appear immune to orange rust [*Gymnoconia nitens* (Schwein.) F. Kern and H.W. Thurston.] and double blossom/rosette [*Cercosporella rubi* (Wint.) Plakidas]. The bloom period of the new cultivar averages 2 to 4 days earlier than the cultivar Ouachita.

Fruit of the 'Natchez' cultivar begins ripening 7 days earlier than the fruit of the cultivar Ouachita, and both have a similar fruiting period with average 35–40 days. Average first ripening date is June 3 in West-Central Arkansas. Fruit yields of the new cultivar are usually 2.3 to 3.2 kg (5 to 7 lb/plant) and are usually comparable to Ouachita cultivar at all test locations. Yields are consistent from year to year.

The fruit are long and cylindrical in shape, bright glossy black in color and very attractive. The fruit are large (8–9 g) and 1.5 to 2.0 g larger than the size of the fruit of the Ouachita cultivar. Fruit size of the new cultivar is maintained well throughout the entire harvest season. The new cultivar exhibits excellent fruit fertility with full drupelet set in contrast to Ouachita, which has slight drupelet sterility on some berries. The fruit is very firm at maturity, rating near that of Ouachita, Apache (U.S. Plant Pat. No. 11,865), and Navaho (U.S. Plant Pat. No. 6,679) cultivars. Storage ability of fresh fruit of the new cultivar is comparable to that of Navaho, Apache, and Ouachita cultivars.

The fresh fruit rates good in flavor, being comparable to that of Arapaho (U.S. Plant Pat. No. 8,510) cultivar and slightly lower in rating than the fruit of Navaho. The flavor is sweet and mildly acidic, with a distinct blackberry aroma. The soluble solids concentration averages 9.5% on shiny black fruit, higher than fruit of Arapaho (7.7%) and lower than fruit of Ouachita (9.8%) and Navaho (10.1%). Dry seed weight averages 4.2 mg/seed, and seeds are comparable to those of Ouachita.

Fruit clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Colour Chart designations. Where dimensions, sizes, colors and other characteristics are given, it is to be understood that such characteristics are approximations of averages set forth as accurately as practicable.

Plants used for botanical data were three years old and grown in a fine sandy loam soil with trickle irrigation at the Fruit Research Station near Clarksville, Ark. The plants were fertilized annually with nitrogen fertilizer, primocanes tipped at approximately 45 inches, and grow in a hedgerow training system. Weeds were controlled with pre- and post-emergence herbicides. A single application of liquid lime sulfur was applied to the plants at budbreak, but not other fungicides were applied. The descriptions reported herein are from specimens grown at Clarksville, Ark. unless otherwise noted.

Plant:

*Size.*—Medium.

*Growth habit.*—Vigorous, with moderate suckering from crowns, moderate suckering from roots, canes erect to semi-erect.

*Productivity.*—High and for duration of five weeks; consistent from year to year. Yields consistently range from 2.3 to 3.2 kg (5 to 7 lb/plant), comparable to Ouachita (U.S. Plant Pat. No. 17,162).

*Cold hardiness.*—Hardy to −14° C. (7° F.), comparable to Ouachita.

*Canes.*—Thornless, erect to semi-erect. Floricane (dormant or winter cane) diameter: base 1.85 cm, midpoint 1.38 cm, terminal 1.12 cm. Primocane (current season cane, late season) diameter: base 1.71 cm, midpoint 1.41 cm, terminal 0.56 cm. Floricane internode length: base 4.43 cm, midpoint 5.20 cm, terminal 2.36 cm. Primocane internode length: base 2.80 cm, midpoint 3.25 cm, terminal 4.0 cm. Floricane color: base-Greyed Orange Group (166A) over Yellow Green Group (144A); midpoint-Yellow Greyed Orange Group (166A) over Yellow Green Group (144A); terminus-Greyed Orange Group (166A) over Yellow Green Group (144A). Primocane color: base-Greyed-Orange Group (176A) over Green Group (143C); midpoint-Greyed-Orange Group (176A) over Green Group (143C); terminus-Greyed-Purple Group (183A) over Green Group (143C). Date of primocane emergence: April 12.

*Disease resistance.*—Moderate resistance to anthracnose; no orange rust or double blossom/rosette observed on plants in trial plots where these diseases were present on other cultivars.

Foliage:

*Primocane.*—Leaves — Large. Mature compound leaf width 15.58 cm; length 17.36 cm. Leaflet: Width 6.32 cm; length 10.88 cm; shape cordate with acuminate apex and cordate base; margin serrated, serration teeth length 0.38 cm, and width at base 0.29 cm; very light pubescence on abaxial surface. Number of leaflets per compound leaf: 5. Color: Base abaxial-Green Group (137A); adaxial-Green Group (137A); midpoint abaxial-Green Group (137A); adaxial-Green Group (137A); terminal abaxial-Green Group (137A); adaxial-Green Group (137A). Petioles — Length: 5.86 cm. Color: Yellow Green Group (146B).

Petiolules — Length: 2.74 cm. Color: Green Group (146B). Stipules — Length: 1.01 cm. Width: 0.064 cm.

*Floricane.*—Leaves — Medium. Mature compound leaf width 7.93 cm; length 8.97 cm. Leaflet: width 4.33 cm; length 6.63 cm; shape cordate, with acuminate apex and cordate base; margin serrated, with serration teeth length 0.44 cm and width at base 0.49 cm; light pubescence on abaxial. Number of leaflets per compound leaf: 3. Color: base abaxial-Yellow Green Group (148B); adaxial-Yellow Green Group (146A); midpoint abaxial-Yellow Green Group (148B); adaxial-Yellow Green Group (146A); terminal abaxial-Yellow Green Group (148B); adaxial-Yellow Green Group (146A). Petioles — Length: 2.47 cm. Color: Yellow-Green Group (146C). Petiolules — Length 0.63 cm. Color: Yellow-Green Group (146C). Stipules — Length: 0.44 cm. Width: 0.21 cm.

Flowers:

*Date of bloom.*—First — Julian 108 (April 17); 50% — Julian 115 (April 24); Last — Julian 129 (May 8).

*Blossom color.*—White Group (155D).

*Reproductive organs.*—Stamens — erect, numerous. Pistils — numerous. Pollen — normal and abundant. Self fertile.

*Flower diameter.*—3.16 cm.

*Petal size.*—Length: 1.63 cm. Width: 1.38 cm.

*Number flowers per cluster.*—Mean of 7 with range of 4 to 10.

*Number of petals per flower.*—6.

*Number of sepals per flower.*—5 to 6.

*Peduncle length.*—1.83 cm.

*Peduncle color.*—Yellow-Green Group (146B).

*Cyme type.*—Elongate simple cyme.

Fruit:

*Maturity.*—Early season, 7 days before Ouachita. Average first ripe date is June 3. Average period of ripening is June 3 to July 11.

*Size.*—Large, average 9.4 g, uniform. Diameter: Fruit at primary position on inflorescence: equator 2.11 cm, base pole 2.26 cm, terminal pole 1.90 cm; fruit at secondary positions on inflorescence: equator 2.13 cm., base pole 2.20 cm, terminal pole 1.85 cm. Length (Primary fruit) 3.64 cm.

*Shape.*—Long, cylindrical, uniform.

*Color.*—Glossy black; Black Group (202A).

*Drupelet size.*—Medium, 0.51 cm.

*Seed size.*—Length 0.37 cm, width 0.212 cm, 0.01 g (dry wt., individual seed).

*Soluble solids.*—9.4%.

*pH.*—3.05 (as measured by pH meter on undiluted juice from a sample of 25 fully-ripe berries).

*Acidity.*—0.94 g citric acid/100 ml.

*Processed quality.*—Not evaluated in processing.

*Uses.*—Fresh is main use but can be processed for jellies, jams, juice, wine.

The variety: The most distinctive features of the variety are its high yields, large fruit size, good fruit quality, early season fruit ripening, prolific fruiting row establishment, and healthy plants.

I claim:

1. A new and distinct cultivar of blackberry plant named 'Natchez', substantially as illustrated and described.

* * * * *